United States Patent
Pham

(10) Patent No.: US 7,759,117 B2
(45) Date of Patent: *Jul. 20, 2010

(54) USE OF DEPTH FILTRATION IN SERIES WITH CONTINUOUS CENTRIFUGATION TO CLARIFY MAMMALIAN CELL CULTURES

(75) Inventor: Christine Y. Pham, San Diego, CA (US)

(73) Assignee: Biogen Idec Inc., Cambridge, MA (US)

( * ) Notice: Subject to any disclaimer, the term of this patent is extended or adjusted under 35 U.S.C. 154(b) by 595 days.

This patent is subject to a terminal disclaimer.

(21) Appl. No.: 11/616,772

(22) Filed: Dec. 27, 2006

(65) Prior Publication Data

US 2007/0267360 A1    Nov. 22, 2007

Related U.S. Application Data

(63) Continuation of application No. 10/871,261, filed on Jun. 21, 2004, now Pat. No. 7,157,276.

(60) Provisional application No. 60/479,910, filed on Jun. 20, 2003.

(51) Int. Cl.
*C12S 3/14* (2006.01)
(52) U.S. Cl. .................. 435/325; 435/243; 435/803; 210/787; 210/767
(58) Field of Classification Search ............... None
See application file for complete search history.

(56) References Cited

U.S. PATENT DOCUMENTS

| | | | |
|---|---|---|---|
| 4,952,127 | A | 8/1990 | Schmeisser et al. |
| 5,451,660 | A | 9/1995 | Builder et al. |
| 7,157,276 | B2 | 1/2007 | Pham |
| 2005/0069979 | A1 | 3/2005 | Zeng et al. |

FOREIGN PATENT DOCUMENTS

| | | |
|---|---|---|
| EP | 0 359 900 | 5/1993 |
| JP | 01 215293 | 8/1989 |
| JP | 05 000232 | 1/1993 |
| WO | WO 03/045995 | 6/2003 |
| WO | WO 03/045996 | 6/2003 |
| WO | WO 03/046162 | 6/2003 |

OTHER PUBLICATIONS

Ambler C et al., "The theory of scaling up laboratory data for the sedimentation type centrifuge," *J Biochem Microbiol Technol Eng*, 1959, 1:185-205.
Borgstrom L et al., "Pressure drop for flow in channels subjected to strong system rotation," *Applied Scientific Research*, 1994, 53:35-50.
Kempken R et al., "Assessment of a disk-stack centrifuge for use in mammalian cell separation," *Biotechnol Bioeng*, 1995, 46:132-138.
Leung WW-F, *Industrial Centrifugation Technology*, McGraw-Hill Professional, 1998, pp. 165-191, 211-245.
Maybury, J et al., "The use of laboratory centrifugation studies to predict performance of industrial machines: studies of shear-insensitive and shear-sensitive materials," *Biotechnol. Bioeng*, 2000, 67:265-273.
Tebbe H et al., "Lysis-free separation of hybridoma cells by continuous disk stack centrifugation," *Cytotechnology*, 1996, 22:119-127.
Singhvi et al., BioPharm., vol. 9, No. 4, 1996, pp. 1-8.
Reider et al., Current Protocols in Cell Biology, print publication, Jul. 2000, John Wiley & Sons, Inc. pp. 1-25. http://www.mrw.interscience.wiley/com/cp/cpcb/articles/cb037/sect2-fs.html accessed Apr. 14, 2005.
European Search Report, Application No. EP 05 76 8196, dated Jul. 9, 2007, 2 pages.

*Primary Examiner*—Allison M Ford
(74) *Attorney, Agent, or Firm*—Sterne, Kessler, Goldstein & Fox P.L.L.C.

(57) ABSTRACT

Methods for clarification of cell samples using centrifugation in combination with depth filtration.

20 Claims, 12 Drawing Sheets

US 7,759,117 B2

USE OF DEPTH FILTRATION IN SERIES WITH CONTINUOUS CENTRIFUGATION TO CLARIFY MAMMALIAN CELL CULTURES

RELATED APPLICATIONS

This is a continuation of U.S. patent application Ser. No. 10/871,261, filed Jun. 21, 2004, which claims priority to U.S. Prov. Patent Appl. No. 60/479,910, filed on Jun. 20, 2003, the contents of both which are incorporated herein in their entirety.

FIELD OF THE INVENTION

The present invention generally relates to methods for solid-liquid separation, for example, separation of cells and cellular debris in a biological sample to thereby prepare a clarified, cell-fee sample. The method is useful as a purification step when isolating proteins secreted by cells in culture, for example, secreted therapeutic proteins.

SUMMARY OF THE INVENTION

The present invention provides methods for clarification of cell samples using centrifugation and depth filtration. For example, the methods are useful for clarification of bacterial cell cultures or mammalian cell cultures. The cell cultures can initially comprise a cell suspension, a cell slurry, or a cell culture, including cultures of at least about 2,200 L, or at least about 15,000 L. For clarification of large cell cultures, an anti-foaming agent can be used. According to the disclosed methods, centrifuging is performed using a gravitational force within the range of about 8,000×g to about 15,000×g. These methods can result in a separation efficiency of at least about 95% following the centrifuging step and a centrate that is substantially free of cells and debris greater than about 2 µm. For depth filtration, the filtration means can include one or more filters, for example, a depth filter and one or more polishing filters. In particular uses, the final filter has a pore size of about 0.1 µm or about 0.2 µm.

DESCRIPTION OF THE INVENTION

Figure 1:
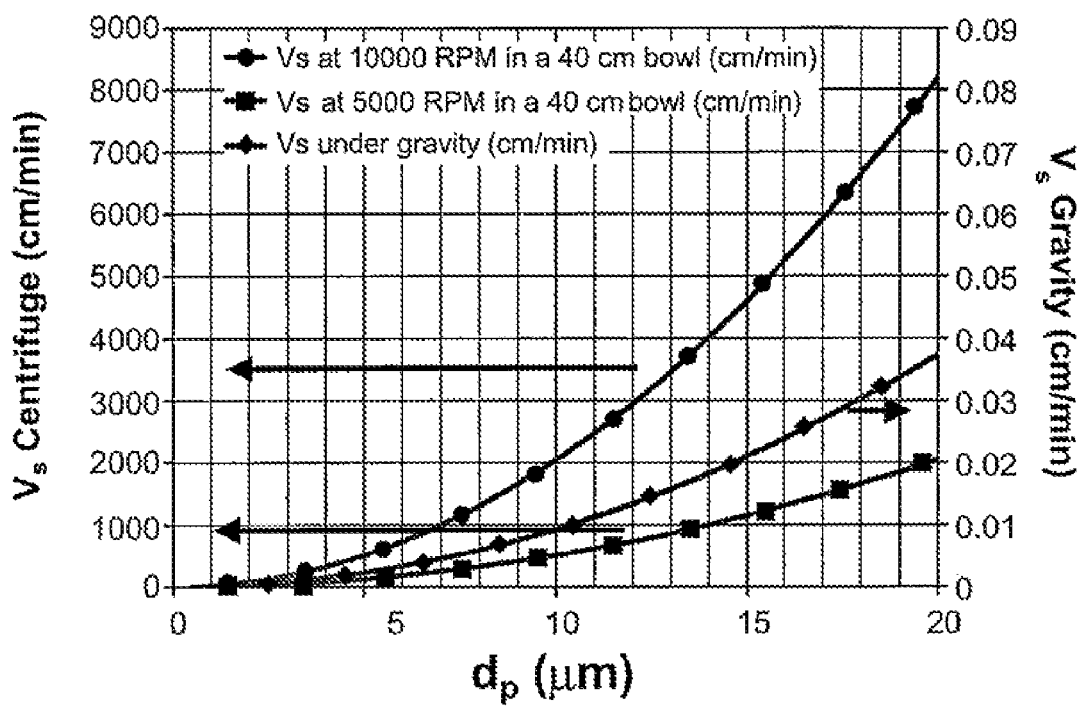
FIG. 1 is a line graph that depicts setting velocity of CHO cells of various size under gravity and in centrifugal fields.

The present invention provides methods for solid-liquid separation using centrifugation in combination with depth and membrane filtration. The combination approach enables rapid separation of large-scale sample suitable for industrial and clinical applications.

The term "solid-liquid sample" refers to any sample including separable solid and liquid phases, wherein a product of interest is substantially in the solid phase or in the liquid phase. Representative solid-liquid samples include suspensions, slurries, cell cultures, etc.

According to the method, a solid-liquid sample is centrifuged to separate a solid phase and a liquid phase, also called a centrate. The centrifugation step is performed to using parameters to achieve a substantially filterable centrate. Typically, the centrifugation step achieves separation of at least about 95% of the solid phase, for example, greater than about 96%, greater than about 97%, greater than about 98%, or greater than about 99%.

Representative centrifugation equipment and techniques are known in the art, for example as described by Kempken et al. (1995) *Biotechnol Bioeng* 46:132-138, by Kempken et al. (1995) *J Indus Microbiol* 14:52-7, by Berthold et al. (1994) *Cyotechnology* 15:229-242, and by Tebbe et al. (1996) *Cytotechnology* 22:119-127.

The present invention further provides that a clarified sample is prepared by subsequent application of the centrate to a depth filtration means to thereby remove particulate matter not removed by centrifugation. The depth filtration means can include one or more filters, such as membrane filters, plate filters, cartridge filters, bag filters, pressure leaf filters, rotary drum filters or vacuum filters. As one example, a CUNO 120M10 grade filter effectively removes debris from the centrate.

The disclosed separation method can be adapted for particular applications, i.e. different cell samples, by selecting appropriate operating conditions, such as normalized loading, g-force, feed temperature, filter grades and sample volumes. For example, centrifugation of mammalian cells is effectively performed using a normalized loading of about $1\times10^{-8}$ m/s and a gravitational force of about 8,000×g. Gravitational force is also effective within the range of about 8,000×g to about 15,000×g, for example within the range of about 8,000×g to about 12,000×g, or within the range of about 8,000×g to about 10,000×g, or within the range of about 10,000×g to about 15,000×g, or within the range of about 12,000×g to about 15,000×g, or within the range of about 10,000×g to about 12,000×g. Normalized loading may be effective at any particular value by varying the above-noted operating conditions. For industrial and clinical applications, large volume samples can be used, including 15,000 L and 2,200 L samples.

The disclosed methods are also useful for clarification of a cell sample, such as animal and bacterial cell samples. For example, secreted protein products arising from cell cultures are prepared for purification by collection of the culture medium, i.e. by removal of cells and cellular debris the culture. The secreted protein products can be native proteins or recombinantly produced proteins.

EXAMPLES

The following examples are included to illustrate modes of the invention. Certain aspects of the following Example are described in terms of techniques and procedures found or contemplated by the present inventor to work well in the practice of the invention. The example illustrates standard laboratory practices of the inventor. In light of the present disclosure and the general level of skill in the art, those of skill will appreciate that the following example is intended to be exemplary only and that numerous changes, modifications, and alterations can be employed without departing from the scope of the invention. Abbreviations used in the Examples are defined in Table 11.

Example 1

Clarification of CHO Cell Suspensions Using a Continuously Operated Disc-Stack Centrifuge Centrifugation is a well-established, continuously operated method for solid-liquid separation in biotechnology. While bacterial and most and foremost yeast suspensions are separated using centrifuges on the very large scale, the use of continuous centrifugation has only recently been discussed for mammalian cell systems. Filtration equipment for centrifugation of 15,000 L samples are bulky and present substantial operational costs, including time costs for filter installation, cleaning, and disposal. These practical considerations are addressed by the disclosed methods for solid-liquid separation of high volume cell suspensions.

There are three major points of concern, which are specific to the separation of mammalian cells in continuous centrifuges. First, shear forces in the centrifuge may damage viable or non-viable cells and lead to the generation of small debris particles. The cell damage may result in release intracellular compounds (host cell proteins, DNA, proteases), which could increase the impurity load of the product pool. Second, mammalian cell suspensions are characterized by a wide distribution of particle sizes (40 µm to sub-micron). The size of the smallest particle which can be effectively removed by centrifugation needs to be determined. Downstream filtration steps (i.e., post-centrifugation steps) are needed to increase centrate clarity to a level suitable for chromatography. Third, rapid throughput for clarification of a cell culture suspension is needed, for example a reasonable harvest time of about 3 hours. The clarification method can be adapted for cell culture variations (cell concentration, density and viscosity of the feed, viability of the culture).

An initial feasibility study was performed using a rented disc stack centrifuge, a SC-6 separator from Westfalia. The machine is sized to operate at volumetric flows between 60 and 1000 L/hour, and therefore was well suited to clarify suspensions produced by a 200 L bioreactor. Three test runs were performed in total with the following main objectives:

(1) To evaluate the general compatibility of a large scale cell suspension with a continuous disc stack centrifuge in terms of particle removal and cell damage;

(2) to determine which filtration steps are required downstream of the centrifuge prior to application of the centrate to the first chromatography column.

(3) to find a suitable window of operation for estimation of centrifuge size required to clarify cell suspensions at production scale and for determination of a centrifugation filtration combination setup for clarifying 2,200 and 15,000 L of cell suspension.

I. Sedimentation of Particles in Viscous Fluids

When a spherical particle of diameter d settles in a viscous liquid under earth gravity g, its terminal settling velocity $V_s$ is determined by the weight of the particle-balancing buoyancy and the viscous drag on the particle in accordance to Stoke's law.

$$V_s = \frac{1}{18} \cdot \frac{(\rho_s - \rho_l) \cdot d^2}{\eta} \cdot g \quad (1)$$

In the rotating flow of a centrifuge, equation (1) is modified by the "centrifugal gravity" $G = \Omega^2 \cdot r$, with $\Omega$ representing the angular speed (equal to $2 \cdot \pi$ times the rotational rate N), r the radius of the centrifuge bowl, $\eta$ the fluid viscosity and $\rho$ the density of suspension (s) and fluid (l).

$$V_s = \frac{1}{18} \cdot \Omega^2 \cdot r \frac{(\rho_s - \rho_l) \cdot d^2}{\eta} \cdot g \quad (2)$$

In order to achieve a good separation of particles in a centrifugal field, a combination of some of the following conditions is required: high centrifuge speed, large particle size, large density difference between solid and liquid, large bowl radius, and small viscosity.

At the specific example of harvesting CHO cell suspensions, some limitations can be identified: mammalian cells show a wide distribution of cell size, additionally some processes may harvest cells at comparatively low viability. The suspension to be clarified therefore contains viable (10-20 µm diameter) and non-viable (4-10 µm diameter) cells, as well as cell debris (sub-micron to 4 µm diameter). This wide size distribution prevents centrifugation to remove all particles from the suspension, and a decision has to be made as to the smallest particle which can be removed under reasonable process conditions. FIG. 1 is a visual presentation of this problem. With an average density of mammalian cells of 1030 kg/m³, a density of a CHO cell suspension of 1000 kg/m³, and a viscosity of the suspension of 1.05 mPa·s the sedimentation velocity of cells of different diameter is shown by the red line. Even very large cells of 20 mm diameter settle only at 0.4 cm/min, debris particles of 1 µm settle at 0.0001 cm/min. Using a 40 cm diameter bowl centrifuge at 10,000 RPM increases the settling velocity dramatically, but particles smaller than 1 µm still settle at unreasonably small velocity. Therefore, centrifugation does not remove all particles, and filtration steps downstream of the centrifuge are required to remove very small particles.

High centrifuge speeds improve the settling, but they also lead to a high acceleration of the cells in the centrifugal field, which in turn may lead to cell damage. Damaged cells may break down into small debris particles and make the separation more problematic due to the size removal constraints discussed above. The bowl radius cannot be increased indefinitely, because an increase in bowl diameter at maintained rotational rate increases the wall stress. For material stability reasons, there is a maximal bowl radius that can be used in high-speed centrifuges. Density difference and viscosity of CHO suspensions can be considered to be favorable, since the cell concentration in a CHO suspension is comparatively low. Running the separation at cell culture temperature (35° C.) is beneficial, since it reduces the viscosity of the suspension.

II. Disk Centrifuges

Figure 2:
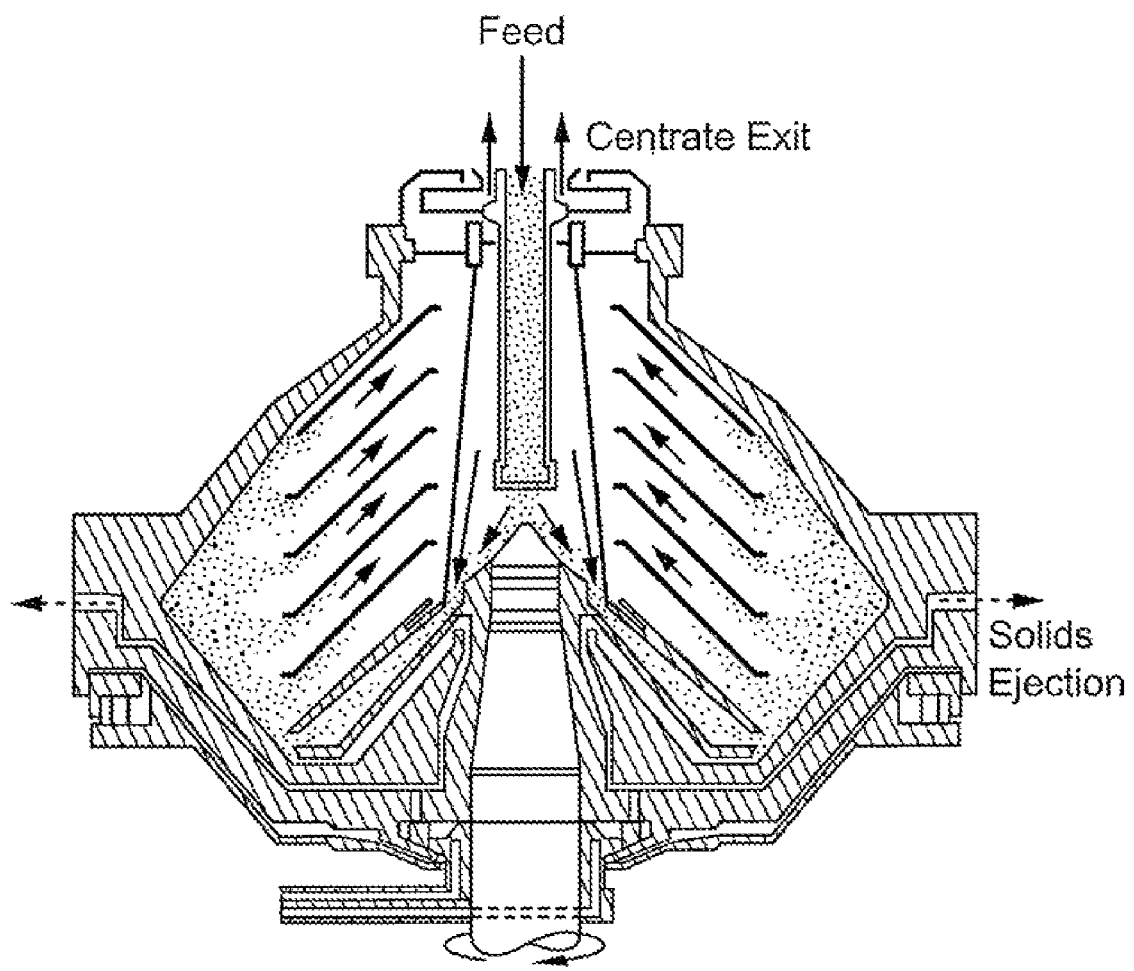
FIG. 2 is a schematic drawing that shows the cross section of a disk stack centrifuge.

One of the most common clarifier centrifuges is the vertically mounted disk machine, as illustrated in FIG. 2. The feed is introduced at the axis of the bowl, accelerated to speed, often by a radial vane assembly, and flows through a stack of closely spaced conical disks. Disk spacing is often between 0.5 to 3 mm in order to reduce the distance required for separating settling particles from the fluid. The disc angle is often between 40 and 50 degrees to facilitate solids transport down the disk surface into the solids holding space.

Figure 3:
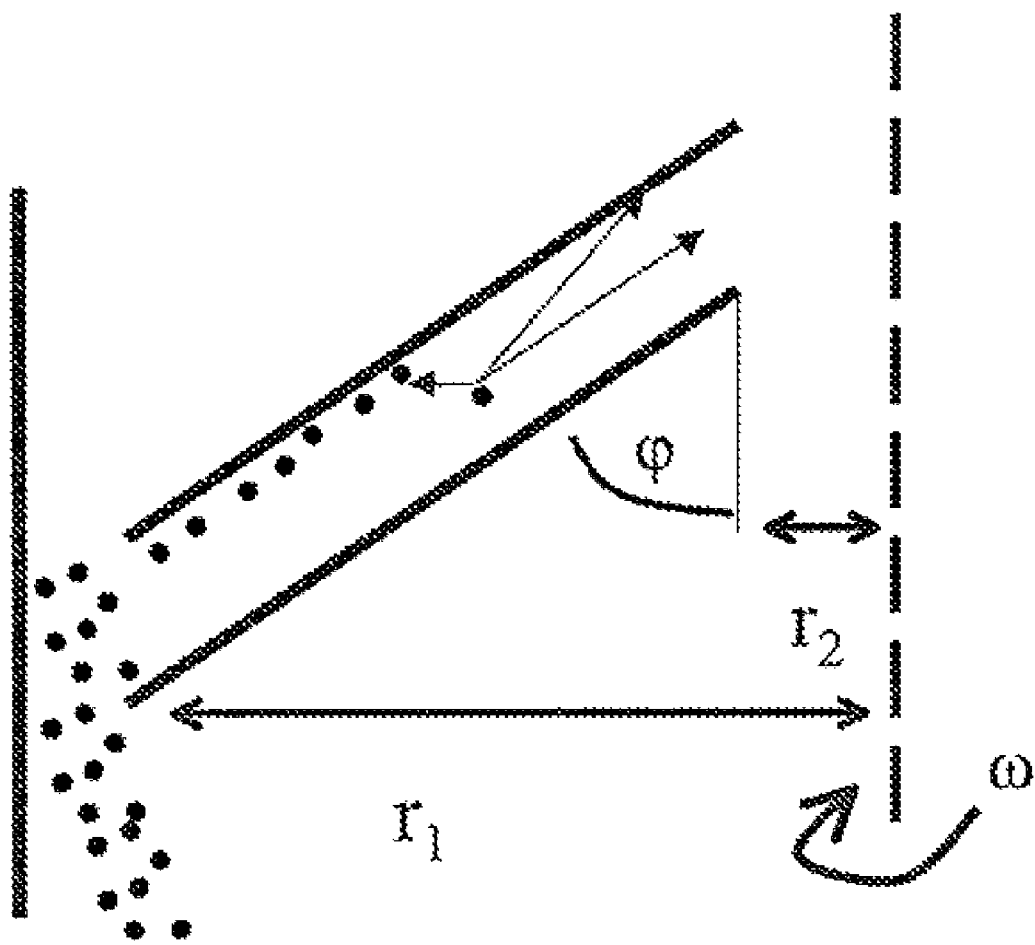
FIG. 3 is a schematic drawing that shows the separation principle of a disk stack centrifuge.

The separating mechanism is as shown in FIG. 3. Solids settle under in the influence of the centrifugal force against the underside of the disks and slide down the disk into the solids hold space. Concurrently the clarified fluid moves up the channel between the disks and leaves the centrifuge via a centripetal pump arrangement. The settled solids are discharged either continuously though nozzles or intermittently through ports at the bowl periphery.

III. Continuous Centrifugal Sedimentation Theory

In order to predict the performance of a continuous centrifuge, the Stokes relationship for settling under gravity (Equation 1) has to be modified for sedimentation in a rotating pool. The settling velocity of a spherical particle of diameter d is then given according to Equation (3):

$$V_s = \frac{dx}{dt} = crd^2 \qquad (3)$$

Assuming plug flow with a uniform distribution of fluid velocity across the pool, the mean axial velocity of a particle traveling from the surface at radius $r_p$ to the bowl wall $r_b$ is calculated according to Equation (4):

$$u = \frac{dr}{dt} = \frac{Q}{\pi \cdot (r_b^2 - r_p^2)} \qquad (4)$$

The residence time of a particle traveling an axial distance x along the bow with the fluid moving at a volumetric flow Q is according to Equation (6):

$$t = \frac{\pi \cdot (r_b^2 - r_p^2) \cdot x}{Q} \qquad (5)$$

Relating the time it takes for a particle to settle to the time it needs to travel with the bulk flow Q results in Equation (6):

$$\frac{r}{r_b} = \exp\left[-\frac{\pi cx \cdot (r_b^2 - r_p^2) \cdot d^2}{Q}\right] \qquad (6)$$

For a particle traveling the entire bowl length L, Equation (6) is modified to Equation (7) for x=L and r=r*:

$$\frac{r^*}{r_b} = \exp\left[-\frac{\pi cL \cdot (r_b^2 - r_p^2) \cdot d^2}{Q}\right] \qquad (7)$$

The size recovery of particles of diameter d ($Re_d$) is given as in Equation (8):

$$Re_d = \frac{\pi(r_b^2 - r^{*2})}{\pi(r_b^2 - r_p^2)} \qquad (8)$$

As a consequence, the maximum volumetric throughput Q, which still allows a certain size recovery $Re_d$, with $V_{gd}$ representing the settling velocity under gravity (1 g) is given according to Equation (9):

$$Q = V_g \cdot A = V_{gd} \cdot \left\{\frac{2\pi\Omega^2 L}{g} \cdot \frac{r_p^2 - r_b^2}{\ln[1 - Re_d(1 - r_p^2/r_b^2)]}\right\} \qquad (9)$$

where A represents the equivalent settling area of the centrifuge under the particular operating conditions. It is a function of bowl radius, settling depth, operating speed, as well as of the size recovery required. The physical parameters of the suspension, i.e. particle size, density and viscosity, are not contained in A, they are captured by the settling velocity of the particle under gravity ($V_{gd}$). When the size recovery is set to 50%, Equation (9) becomes the Ambler equation (Equation (10)), with $\Sigma_{50\%}$ representing the area equivalent for 50% size recovery.

$$\sum_{50\%} = \frac{1}{2} \cdot A_{Red=50\%} = \left\{\frac{\pi\Omega^2 L}{g} \cdot \frac{r_p^2 - r_b^2}{\ln[1 - Re_d(1 - r_p^2/r_b^2)]}\right\} \qquad (10)$$

In an approximation, the Ambler equation simplifies to Equation (11):

$$\sum_{50\%} = \frac{\pi\Omega^2 L}{g} \cdot \frac{r_b^2 - r_p^2}{2\ln(r_b/r_p)} \qquad (11)$$

For disk stack centrifuges, a similar equation can be developed for $\Sigma_{50\%}$ (Equation (12)):

$$\sum_{50\%} = \frac{2\pi\Omega^2 \cdot (N-1)(r_o^3 - r_i^3)}{3g \cdot \tan\varphi} \qquad (12)$$

where N is the number of disks in the stack, $r_o$ and $r_i$ are the outer and the inner radius of the conical disks, and $\phi$ is the conical half angle. $\Sigma$ essentially represents a combination of the size of the centrifuge and the operating conditions in terms of speed. For scale-up, the relationship of $\Sigma$ and the volumetric throughput (Q/$\Sigma$), which is measured in m/s, is kept constant. If the volumetric throughput, which is required at scale, is known, and small-scale experiments have shown, that a certain $\Sigma$ is sufficient to obtain the required clarity, then the $\Sigma$ required for the large scale centrifuge can be calculated using Equation (13). Alternatively, Σ can be calculated for a given piece of equipment after Equation (12), and the achievable throughput can be calculated for this machine using Equation (13).

$$\frac{Q_2}{\Sigma_2} = \frac{Q_1}{\Sigma_1} = 2V_{gd} \quad (13)$$

Scaling up using Equation (13) has some limitations, since a number of assumptions were made in deriving the throughput equations:
1. Flow in the centrifuge may not be plug flow, velocity gradients may exist;
2. the feed is not immediately accelerated to full g at the feed port, leading to reduced g-force exposure and reduced separation efficiency;
3. Σ only corresponds to 50% size recovery;
4. non-uniform feed distribution at the inlet; and
5. particle settling in the suspension might be hindered at high particle concentration, leading to reduced separation efficiency.

During scale-up these limitations are usually considered by implementing certain correction factors. For large scale centrifuges the correction factor used to estimate the throughput according to Equation (9) is between 0.4 and 0.7, i.e. the real performance of the machine is estimated to be between 40% and 70% of the predicted performance according to the idealized Equation (9).

IV. Technical Specification of the Rental SC-6 Separator

The technical details of the rental SC-6 separator are as follows:

| | |
|---|---|
| Total bowl volume | 1.8 L |
| Sediment holding volume | 0.7 L |
| Max. Bowl Speed | 12,000 RPM |
| Number of disks in stack | 75 |
| Disc angle | 40° |
| outer disk diameter | 0.068 m |
| inner disk diameter | 0.0125 m |

From these data the centrifugal acceleration G (in multiples of g) can be calculated as a function of the bowl speed according to Equation (14):

$$G = \frac{r \cdot \Omega^2}{g} \text{ with } \Omega = 2\pi \cdot bowlspeed \ (s^{-1}) \quad (14)$$

Figure 4:
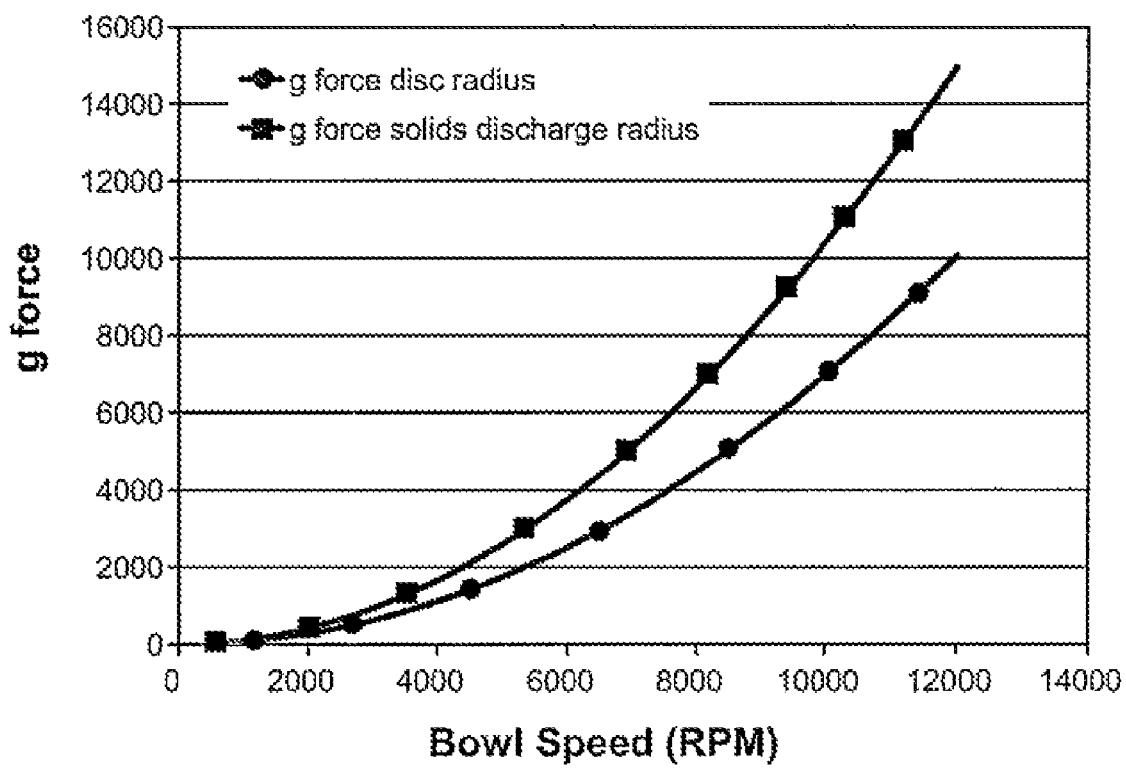
FIG. 4 is a line graph that depicts g force in the SC-6 separator as a function of bowl speed.
Figure 5:
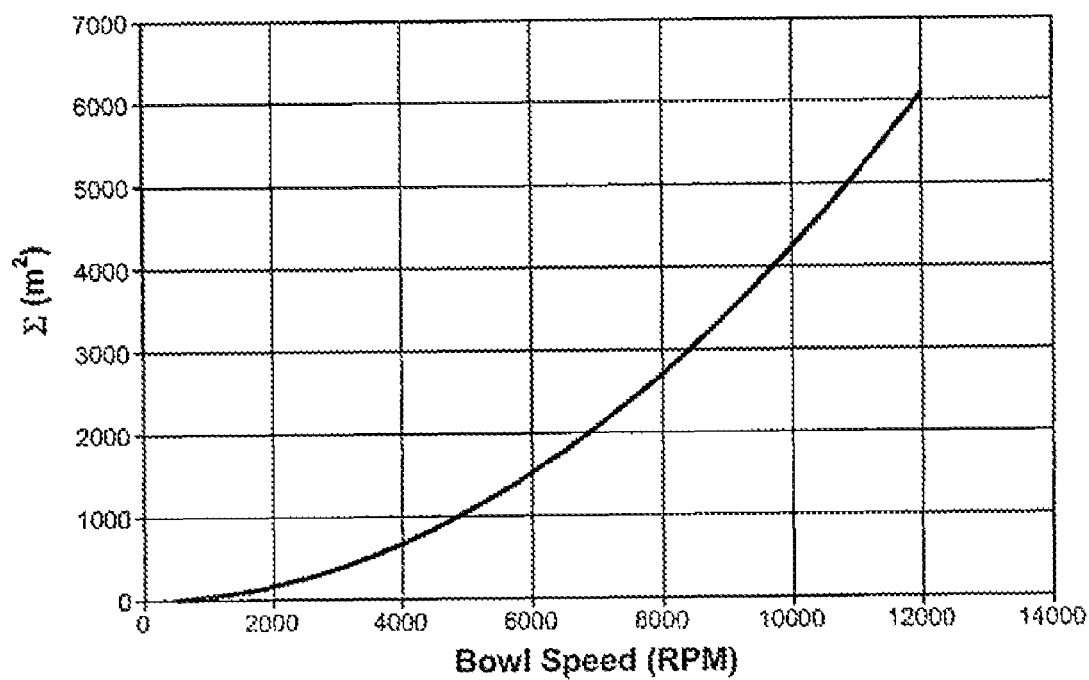
FIG. 5 is a line graph that depicts Σ as a function of bowl speed for the SC-6 separator.

For a disk stack centrifuge G can be calculated based on the outer radius of the disk stack (0.068 m) or using the radius of the solids holding space (0.093 m). FIG. 4 shows the development of G as a function of bowl speed for both cases. The g force can be calculated using the radius of the solids holding space, which is approximately 15,000×g for the highest bowl speed of 12,000 RPM.

V. Operation of the Rental SC-6 Separator

V.A. Theoretical Considerations

Prior to test runs with the SC-6 separator, the performance of the machine was estimated for a range of operating conditions. From Equation (13), the throughput at which a certain particle diameter is separated at 50% size recovery can be calculated from $\Sigma_{50\%}$ and the settling velocity under gravity $V_{gd}$. For the disk stack centrifuge $Q_{max}$ is calculated according to Equation (15):

$$Q_{max} = \frac{d^2 \cdot (\rho_s - \rho_l) \cdot g}{18\eta} \cdot \left\{ \frac{2\pi\Omega^2}{8} \cdot \frac{(N-1)(r_o^3 - r_i^3)}{3 \tan(\varphi)} \right\} \quad (15)$$

Figure 6:
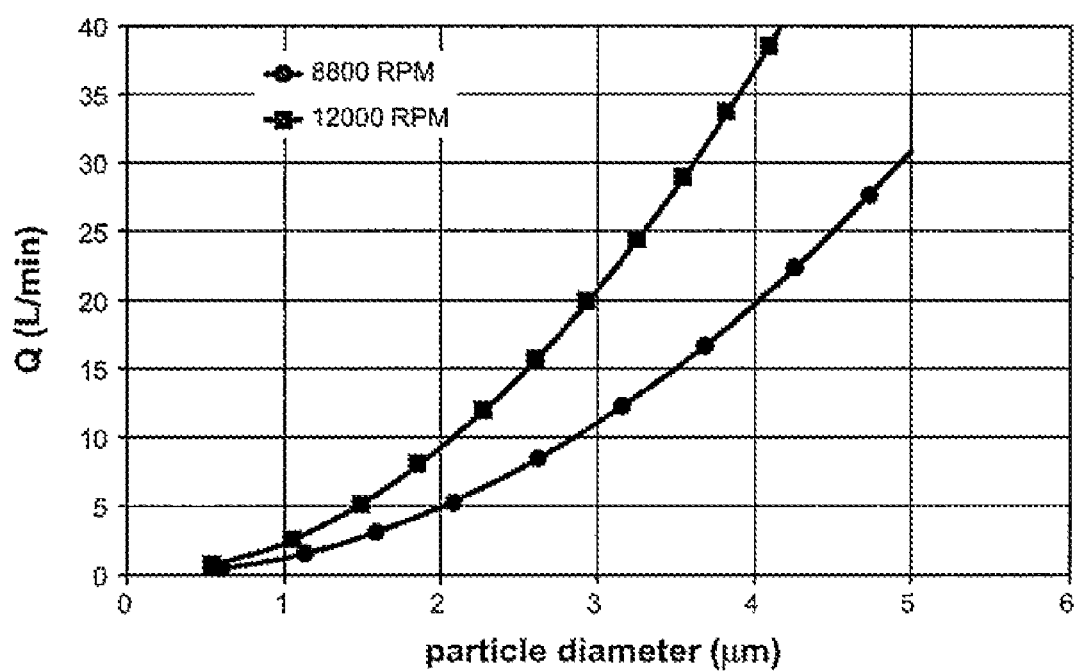
FIG. 6 is a line graph that depicts achievable throughput of the SC-6 separator at 8,000 and 15,000×g (8,800 and 12,000 RPM) as a function of the smallest particle size, which is removed at 50% size recovery.

Using a correction factor of 0.5, which takes into consideration preferred separation of all of the particles from a certain size group, the maximum throughput of the SC-6 separator can be plotted as a function of the smallest particle size to be removed. FIG. 6 shows this plot for 8,800 and 12,000 RPM bowl speed for a wide range of particle sizes. It is evident, that an attempt to remove particles smaller than 1 μm leads to unreasonably low volumetric throughput. The goal of the centrifugation operation is not to remove all particles from a cell suspension, but rather to remove the majority of particles and use a small depth filter assembly for final polishing prior to absolute filtration. Assuming that removal of all particles larger than 2 μm is sufficient to substantially reduce the area required for the final polishing filter, it was calculated that at 8,000×g (8,800 RPM) a throughput of 4.9 L/min is possible. Running the separator at full bowl speed of 12,000 RPM (15,000×g) allows increasing the throughput to 9 L/min. Under these conditions, the separator can be operated at a Q/Σ of 2.5·10⁻⁸ m/s. Since Q/Σ is a significant factor for determining operating conditions, the experimental evaluation of the SC-6 separator was set up such that a range of Q/Σ between 0.9 and 2.8·10⁻⁸ m/s was tested. Given that mammalian cells may respond to variations in the g force used in the separator, Q/Σ was varied by adjusting volumetric flow or by adjusting g force. The general sedimentation theory predicts that increasing the g force increases Σ, which in turn leads to improved separation. In the case of shear sensitive particles, as mammalian cells, increasing g force may lead to increased shear damage and generation of smaller particles that can no longer be separated under the operating conditions chosen.

V.B. Experiment 1

An initial evaluation of the performance of the SC-6 separator included the test conditions shown in Table 1. 280 L of IDEC-114 cell culture suspension were available for separation, and approximately 30 L of suspension each were applied for the eight experimental points. Given that the bowl volume of the SC-6 separator is 1.8 L, application of 18 L of feed (10 liquid residence times) should be sufficient to obtain steady state. However, sedimented cells accumulate in the solids hold-up space (0.7 L), which therefore has to be emptied by partial or total discharge shots. The shots disturb the equilibrium and it is important to observe experimental conditions over several discharge shots. At an estimated packed cell volume of 3% (30 g/L) and assuming that the cells are compacted to approximately 50% wet volume in the solids holding space, 350 g of cells can be held prior to discharge, which corresponds to approximately 12 L of feed volume. The solids were partially discharged after 10 L of feed application by 400 mL shots, which allowed observation of the system for three solids discharges. Feed and centrate samples were taken and analyzed for packed cell volume as well as for particle size distribution. Additionally, the feed and centrate temperature was measured in order to check whether heat generation in the centrifuge exceeded the cooling capacity of the separator's bowl cooling system. In all experiments, the effluent temperature never rose more than one ° C. above the feed temperature.

TABLE 1

| | Initial Test Conditions | | | | | | | |
|---|---|---|---|---|---|---|---|---|
| | Run # | | | | | | | |
| | 1 | 2 | 3 | 4 | 5 | 6 | 7 | 8 |
| G force (×1000 g) | 12 | 15 | 15 | 8 | 8 | 9.6 | 9.6 | 9.6 |
| Q (L/min) | 5.3 | 10.3 | 3.3 | 1.8 | 5.1 | 6.4 | 4.3 | 2.1 |
| Σ (m²) | 4950 | 6172 | 6172 | 3400 | 3400 | 3960 | 3960 | 3960 |
| Q/Σ ($10^{-8}$ m/s) | 1.8 | 2.8 | 0.9 | 0.9 | 2.6 | 2.7 | 1.8 | 0.9 |

Figure 7:
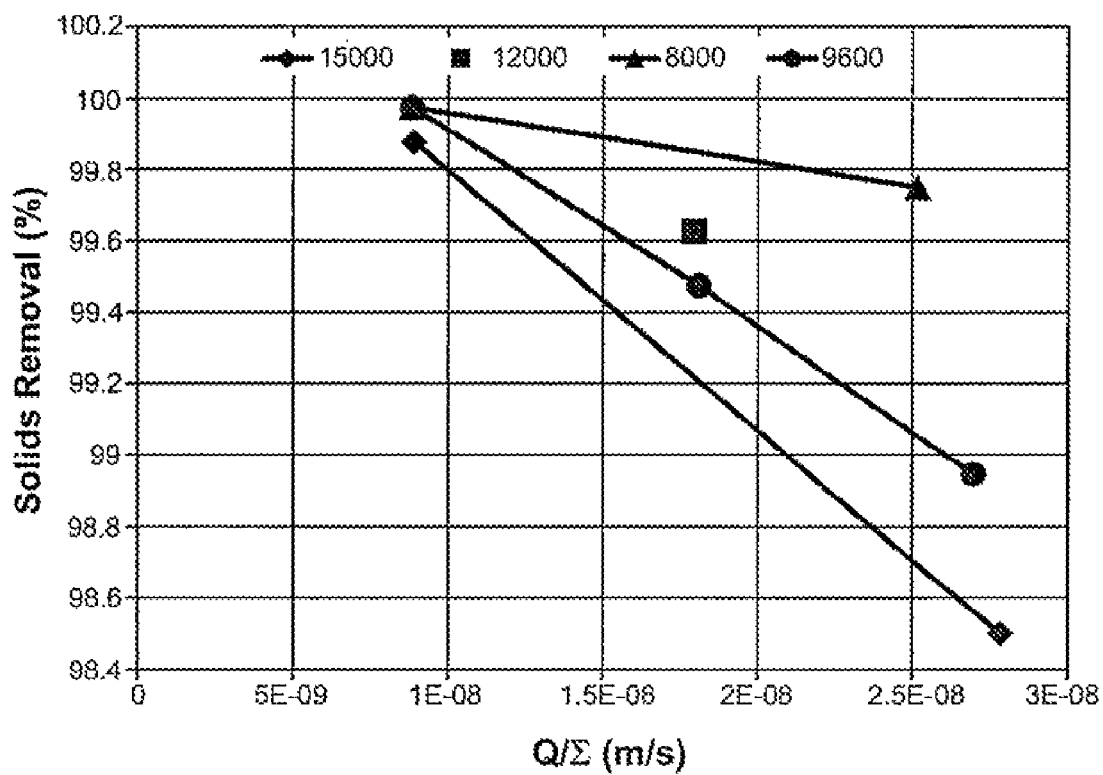
FIG. 7 is a line graph depicting solids removal as a function of Q/Σ and g force.
Figure 8:
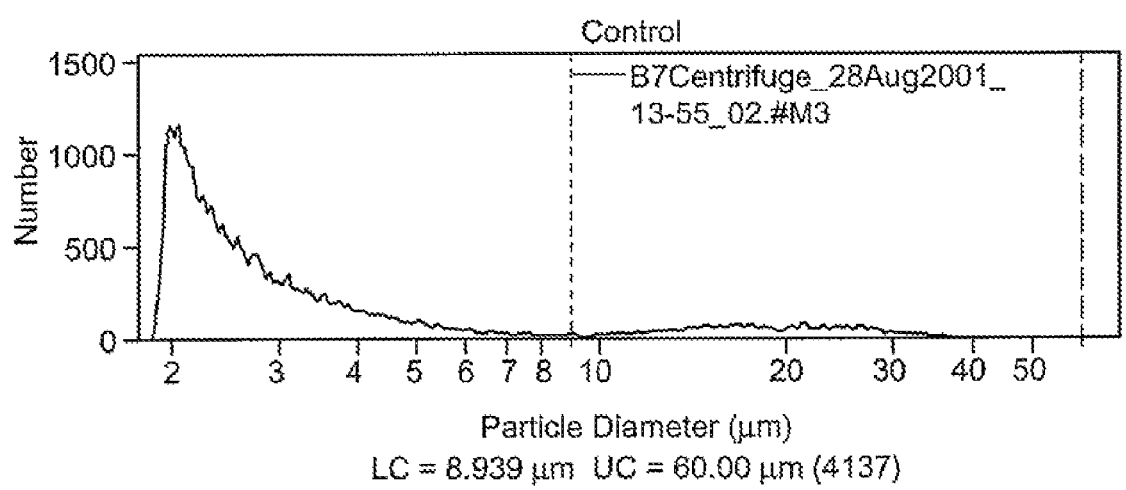
FIG. 8 is a plot of particle size distribution of the IDEC-114 culture, which was used as a feedstock for the centrifugation experiments. The population between 10 and 35 mm represents the viable cells, and the population smaller than 4 mm represents the cell debris. The resolution of the method is 0.6 µm; all particles smaller than this size were not recorded (x-axis at log scale).

The results of the eight test conditions are summarized in FIG. 7. The performance of the solid-liquid separation is usually characterized by ability to remove solids. Solids removal E is defined according to Equation (16):

$$E = \frac{(PCV_{feed} - PCV_{centrate})}{PCV_{feed}} \cdot 100 \qquad (16)$$

where PCV represents the percentage of paced cell volume. FIG. 7 demonstrates that the removal efficiency decreases with increasing challenge to the centrifuge (Q/Σ), i.e., if the throughput to a centrifuge at a given area equivalent is increased, the separation performance will decrease. This behavior is expected and predicted by the sedimentation theory (Equation (15)). The particularities of the mammalian cell system become evident when the g force applied is considered. At low challenge, the g-force does not significantly influence the separation performance. At higher challenges, however, the performance at high g force is substantially reduced. This may be explained by the increased shear damage of the cells at high g, which leads to the generation of fines and a concomitantly reduced separation of the small particles. The data in FIG. 7 shows that operation of the SC-6 at 8,000×g is the preferred option, since this allows running the separator at higher challenge.

Figure 9:
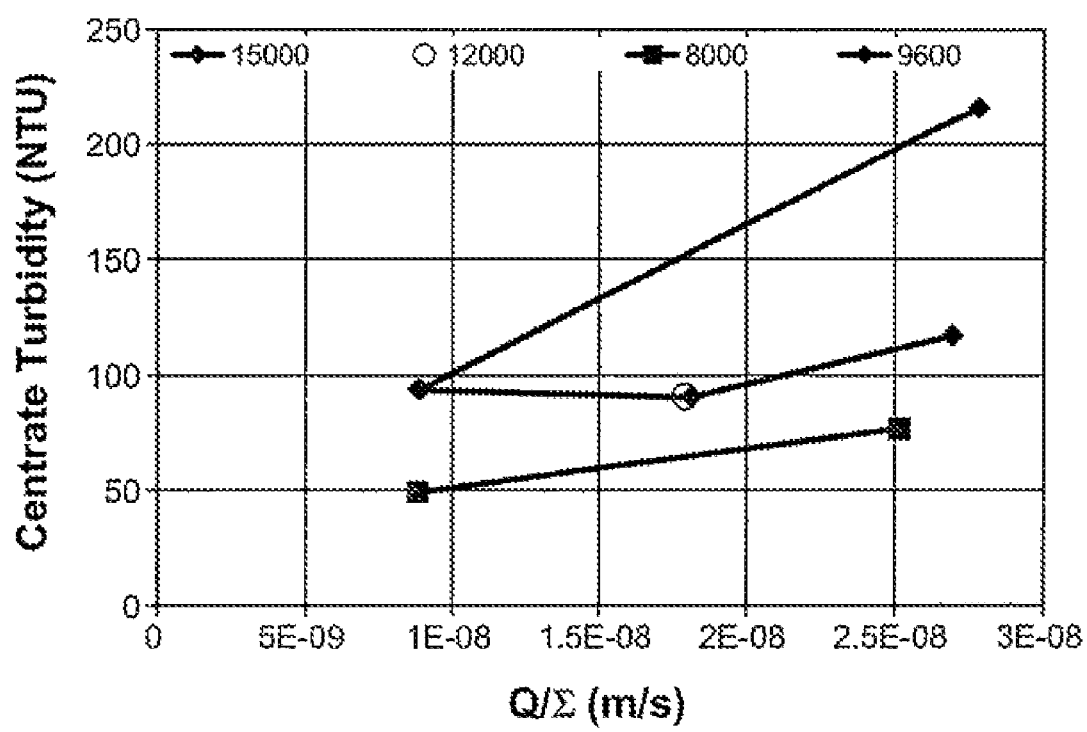
FIG. 9 is a line graph depicting centrate turbidity as a function of operating conditions for the first set of centrifugation experiments (Example 1).

To consider an alternative measurement for the efficiency of the separation, the turbidity of the centrate was measured for the different operating conditions. FIG. 9 plots the centrate turbidity as a function of g force and challenge (Q/Σ). The turbidity gives a much more refined picture of the centrifuge's performance, since it is caused by all particles in the suspension and therefore represents the total particle population in the centrate. FIG. 9 shows that even at low challenge increasing g force leads to the generation of fines, which are not removed as efficiently as the larger particles. This reduction of separation performance due to shear induced cell disruption is not detected using the packed cell density as a performance criterion.

Figure 10:
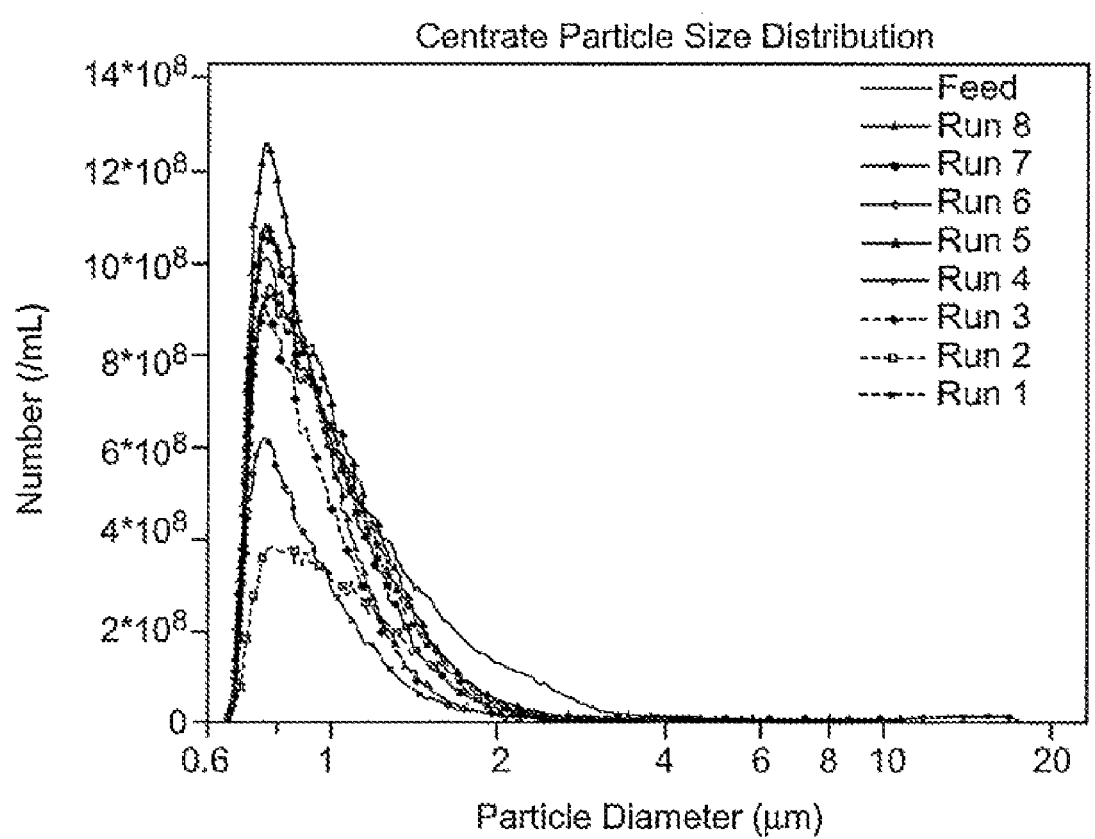
FIG. 10 is a plot of particle size distribution of the centrates obtained during the first centrifugation experiments (run numbers correspond to operating conditions detailed in Example 1).

This is confirmed by the results of the particle size distribution of the different centrates, which is shown in FIG. 10. For greater simplicity, only the particles smaller than 4 μm are shown. The feed contains particles of all sizes, whereas the centrifugation successfully removes all particles larger than 2 μm. Subtle differences in the size distribution can be detected for different operating conditions. Run 4, which was operated at 8,000 g and a low challenge shows substantial removal of particles between 1 and 2 μm, while operation at high g force and high challenge (Run 1 and 2) results in a remarkable shift in the distribution towards larger particles. Therefore, these data also suggest that operation at low g force (preferably 8,000×g) and low challenge ($0.9 \cdot 10^{-8}$ m/s) is preferred for optimal separation performance.

It is interesting to compare these results to the predictions made above. Using the sedimentation theory we predicted that 50% of all particles larger than 2 μm will be removed at a challenge of $2 \cdot 10^{-8}$ m/s and 8,000 RPM (corresponding to approximately 8,000×g). At Q/Σ of $1 \cdot 10^{-8}$ m/s, all particles larger than 2 μm were removed, confirming estimates made the theory explained herein above. The theory predicted an even better performance at high g forces, which was not achieved in practice. Rather, the performance decreased with the g force. This unpredictability reflects peculiarities of the mammalian cell system, wherein shear-induced cell damage leads to a change in particle size distribution, which is not accurately accommodated by the simplified theory.

Since centrifugation cannot deliver a particle-free centrate, polishing and absolute filters need to be installed further downstream. A filter train consisting of a CUNO 60SP depth filter, followed by Pall Ultipor 0.2 μm and 0.1 μm filters was investigated for filter capacity for the centrates resulting from the different experimental conditions. The results of the study are presented in Table 2.

TABLE 2

Results of Experiments to Test Filter Train

| | | | | |
|---|---|---|---|---|
| G force | 15,000 | 15,000 | 8,000 | 9600 |
| Q/Σ (m/s) | $2.8 \cdot 10^{-8}$ | $0.9 \cdot 10^{-8}$ | $0.9 \cdot 10^{-8}$ | $0.9 \cdot 10^{-8}$ |
| Turbidity post CUNO 60 SP depth filter (NTU) | 22 | 11.5 | 11.8 | 18 |
| Ultipor 0.2 μm capacity (L/m²) | 116 | 438 | 265 | 159 |
| Ultipor 0.1 μm capacity (L/m²) | 197 | 178 | 195 | 110 |

The most important finding from these experiments was that the capacities of the absolute filters are very low, in particular in the case of the 0.2 μm filters. Apparently the CUNO 60SP depth filters did not provide sufficient protection for the absolute filters downstream. This is supported by the considerable turbidity of the filtrate of the depth filter. The absolute numbers of the filter capacity would necessitate the installation of huge filter elements downstream of a centrifuge. Based on these data, a 15,000 L culture would require the installation of 65 0.2 μm filter elements of 10" diameter and of 150 0.1 μm filter elements of 10" diameter downstream of the centrifuge. In terms of the influence of the operation conditions (Q/Σ, g force) there was no conclusive influence on the filter performance.

Parallel to the filtration experiments, a control experiment was performed using the same IDEC-114 cell suspension that was clarified using the "conventional" depth filter train (CUNO 10 SP, CUNO 60 SP, Pall Ultipor 0.2 μm, Pall Ultipor 0.1 μm). The capacities of the two absolute filters were comparable to the capacities of the centrifuge centrates under the best operating conditions. The 0.2 μm filter capacity of the control was 497 L/m², while the 0.1 μm filter capacity was 182 L/m². This demonstrates that the IDEC-114 cell culture suspension as such has a low filterability and that centrifugation does not make absolute filtration downstream such a complex and tedious task.

V.B. Experiment 2

Based on the findings from Experiment 1, a second set of centrifugation experiments was performed to identify a filter train with improved filterability. The experimental conditions and the corresponding separation performance are set forth in Table 3.

TABLE 3

Results of Experiments to Test Different Filter Trains

| | Run # | | |
|---|---|---|---|
| | 9 | 10 | 11 |
| G force | 8,000 | 8,000 | 15,000 |
| Q (L/min) | 1.8 | 5.1 | 10.3 |
| Σ (m²) | 3400 | 3400 | 6174 |
| Q/Σ ($10^{-5}$ m/S) | 0.9 | 2.5 | 2.8 |
| Solids recovery (%) | 99.4 | 99.7 | 99.6 |
| Centrate Turbidity (NTU) | 63 | 111 | 344 |

Again the solids recovery appears to be excellent across the bard, the centrate turbidity, however, reveals differences in the separation performance. As in the first set of experiments, operating the centrifuge at low g-force and reduced Q/Σ avoids generation of fines by shear damage and allows a good reduction in the overall turbidity. The centrates were then filtered using various depth filters, which were of finer grade than the original CUNO 60SP filters. The overall intent was to allow better protection of the absolute filters. The turbidities (in NTU) of the respective filtrates are shown in Table 4.

TABLE 4

Filtrate Turbidities

| | Run # | | |
|---|---|---|---|
| | 9 | 10 | 11 |
| CUNO 60-120 SP | 9.2 | 8.1 | 21.3 |
| CUNO 90 SP ZA | 14.2 | 10.6 | |
| CUNO 120M10 grade | 8.6 | | 7.5 |
| Millipore 75 DE | 20.5 | | |
| Millipore 60DE-75DE-RW01 | 8.3 | 6.6 | 14.5 |

Keeping in mind that the turbidity of the original CUNO 60SP filtrates was higher than 10 NTU, using the finer grade filters reduced the turbidity load to the absolute filters. Notwithstanding this effect, the centrifuge operating conditions have a decisive influence on the performance of the depth filters. From the depth filter filtrates resulting from the different centrifuge operating conditions it is clear that operating at low g and low Q/Σ is advantageous.

The Ultipor 0.2 and 0.1 μm filter capacities of the different depth filter filtrates are shown in Table 5. The finer grade depth filters provides improved protection of the 0.2 μm filters. In the best case, the capacity was increased by more than a factor of five. The 0.1 μm filter capacity, however, remained low. As a control, the IDEC-114 suspension was also filtered using conventional techniques and the same feed suspension. Low capacity of the 0.1 μm filter was observed for the control as well. These results suggest that it is the culture suspension which makes 0.1 μm filtration so demanding, i.e., a well operated centrifuge does not deteriorate the absolute filter's capacity compared to the control.

TABLE 5

Filter Capacities

| | Run # | | | |
|---|---|---|---|---|
| | 9 | 10 | 11 | Control |
| CUNO 60-120 SP 0.2 μm capacity | 1996 | | 339 | 2251 |
| CUNO 90 SP ZA 0.2 μm capacity | 600 | 706 | | |
| CUNO 120M10 grade 0.2 μm capacity | 2649 | | 1364 | |
| Millipore 75 DE 0.2 μm capacity | 157 | | | |
| Millipore 60DE-75DE-RW01 0.2 μm capacity | | 1154 | 218 | |
| CUNO 60-120 SP 0.1 μm capacity | 140 | | 173 | 291 |
| CUNO 90 SP ZA 0.1 μm capacity | 78 | 96 | | |
| CUNO 120M10 grade 0.1 μm capacity | 164 | | 178 | |
| Millipore 75 DE 0.1 μm capacity | 168 | | | |
| Millipore 60DE-75DE-RW01 0.1 μm capacity | | 212 | | |

V.D. Experiment 3

A third series of experiments was performed to reduce the 0.1 μm filter requirements. Two lines of thought were pursued. First, it was speculated that the 0.1 μm filters became blocked by fines, which are generated in the centrifuge, either by the inlet shear or by shear forces exerted on the compacted cells in the solids holding space. The latter possibility of cell damage was investigated by using two different solids with discharge volumes of 400 and 250 mL. Smaller discharge volumes require more frequent shots, which in turn reduce the residence time of the sedimented cells in the solids holding space and reduce the overall exposure to compaction stress. If compaction causes cell damage, then reduced shot volumes were predicted to reduce the generation of fines and improve the 0.1 μm filterability. Additionally, in one set of operating conditions the feed was cooled to 10° C. Reducing the temperature is known to make mammalian cells less amenable to shear damage. Therefore, it was expected that the generation of fines would be avoided at reduced temperature. All runs were operated at 8,000×g and Q/Σ of $0.9 \cdot 10^{-8}$ m/s, the solids removal was 99.8% in all cases, which corresponds well to the previous results. The centrate turbidity was 32 NTU for the runs at 37° C., irrespective of the shot volume, which indicated that the residence time in the solids holding space does not impact the generation of fines. The centrate turbidity of the run operated at 10° C. was only 24 NTU, which might indicate that fewer fines were generated due to the increased stability of the cells at reduced temperature. For the centrates, the filter capacity of the CUNO 90-120SP depth filter was determined as 41 L/m². In a conventional depth filtration train, where a CUNO 1-10SP depth filter was used prior to the 90-120SP for the same IDEC-114 culture, the 90-120SP capacity was found to be 400 L/m². Thus, centrifugation makes initial depth filtration obsolete as well as reducing the requirements for the secondary polishing depth filter by 10%. The results of the filterability studies for the absolute filters are shown in Table 6.

TABLE 6

Filterability Assays

| | Run # | | | |
|---|---|---|---|---|
| | 12 | 13 | 14 | Control |
| G force | 8,000 | 8,000 | 8,000 | |
| Q (L/min) | 1.8 | 1.8 | 1.8 | |
| Q/Σ ($10^{-8}$ m/s) | 0.9 | 0.9 | 0.9 | |
| Discharge Volume (mL) | 250 | 400 | 400 | |
| Temperature (° C.) | 37 | 37 | 10 | |
| Turbidity of CUNO 120M10 grade filtrate (NTU) | 5.8 | 5.9 | 6.2 | |
| Ultipor 0.2 µm capacity (L/m²) | 2751 | 2021 | 889 | >2800 |
| Ultipor 0.1 µm capacity (L/m²) | 157 | 141 | 16 | 217 |

None of the modifications was able to improve 0.1 µm filterability, which was comparable to a conventionally filtered control. These problems may be specific to the IDEC-114 cell culture process and not to the centrifugation as and alternative unit operation. The lower temperature, on the contrary, substantially reduced the filterability.

Figure 11:
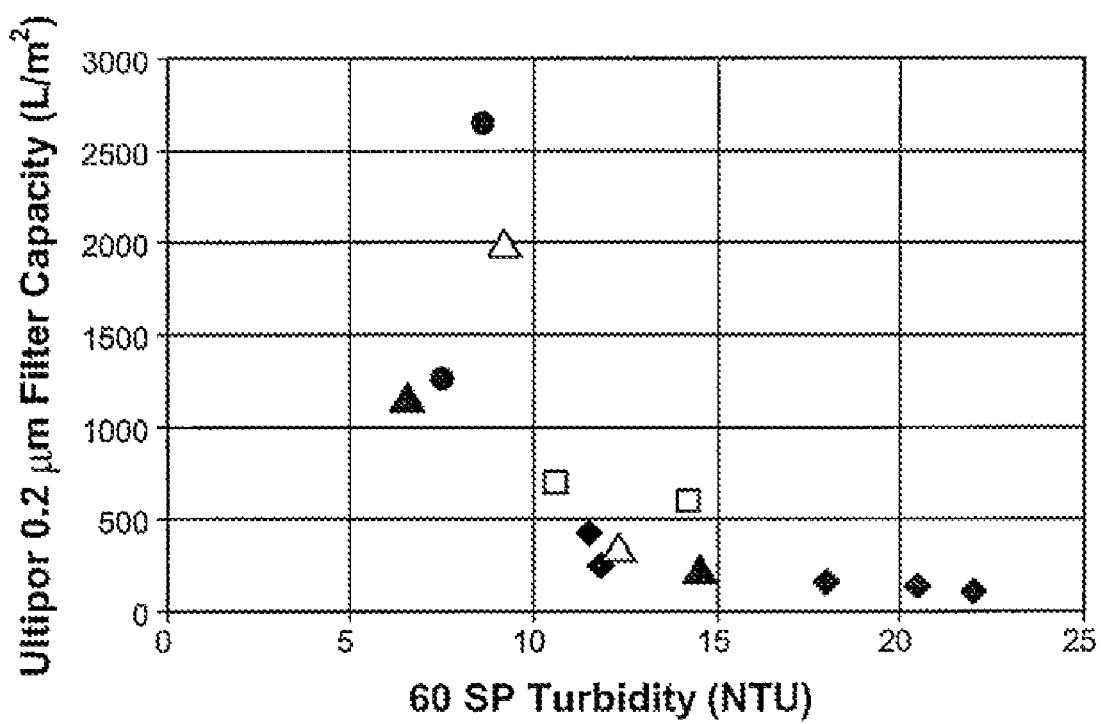
FIG. 11 is a line graph depicting ultipor 0.2 µm filter capacity versus load turbidity.
Figure 12:
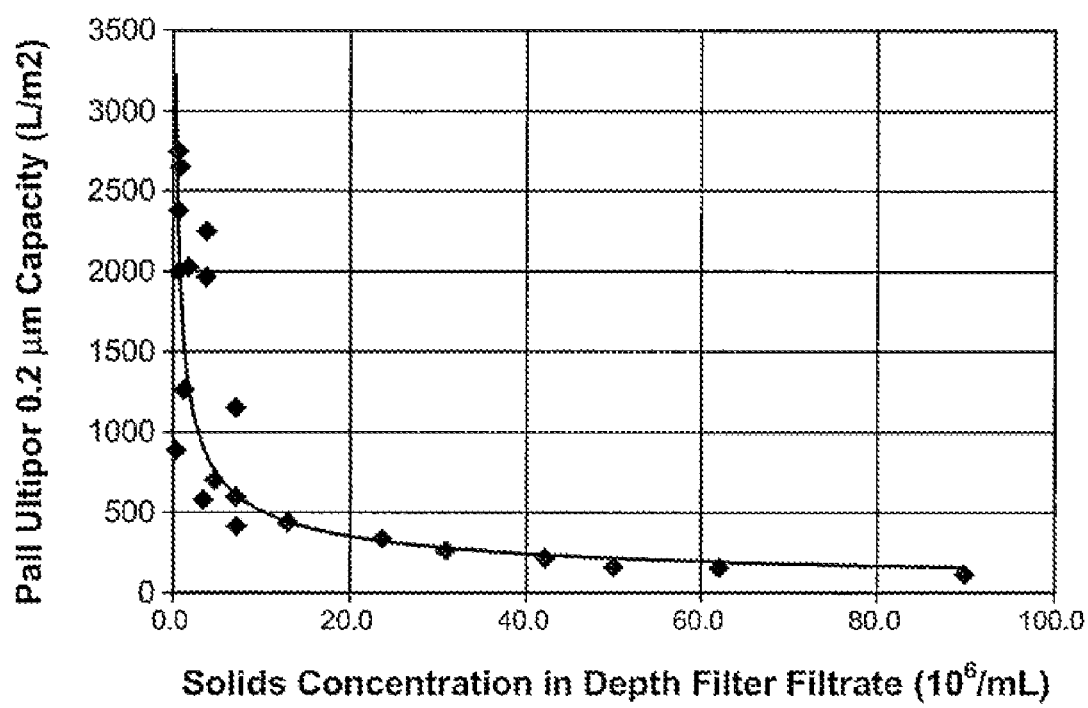
FIG. 12 is a line graph depicting ultipor 0.2 µm filter capacity versus load particle concentration.

Based on the present disclosure, it is possible to estimate the 0.2 µm filterability from either the turbidity or the particle concentration (as found from the particle size distribution). In order to allow a reasonable filter capacity, the turbidity is preferably less than 10 NTU or the particle concentration is preferably below $5 \cdot 10^8$ particle per mL. See FIGS. 11 and 12.

These experimental results point towards operation of a disk stack centrifuge at low g force (8,000×g) and a Q/Σ of approximately $0.9 \cdot 10^{-8}$ m/s. Based on these data we are able to estimate the size of a centrifuge for NIMO (15,000 L culture volume) and NICO (2,200 L culture volume). For comparability, only results obtained using equipment available from Westfalia was used. For the NIMO scale, an appropriate piece of equipment is the CSD 130 clarifier, which has a maximum area equivalent Σ of 130,000 m² at 8,000×g. Using Equation (13), the throughput of this machine was estimated to be $0.9 \cdot 10^{-8}$ m/s, which results in 4200 L/h volumetric throughput and approximately four hours total harvest time. Similarly, a CSC 20 clarifier may be used at NICO sale. At its maximum bowl speed of 8,300 RPM, it operates at approximately 8,400×g and has an area equivalent of 22,000 m². Equation (13) predicts a volumetric throughput of 710 L/h and a three hour harvest time for the optimal run conditions with the SC-6 separator. These calculations demonstrate that the centrifugation conditions established in the initial evaluation fulfill the scheduling requirements of NIMO and NICO scale production.

An additional point of interest is whether the implementation of centrifugation into large-scale harvest procedures is able to reduce the overall cost of solid-liquid separation in comparison to a filtration-only approach. The first step towards such an analysis is an estimate of the filter cost involved in both scenarios. IDEC Purification Process Sciences has performed an initial analysis of the filtration requirements for IDEC-114 clarification. A filtration train was established as shown in Table 7.

TABLE 7

Filtration Train

| Filter | Capacity (L/m²) | Filter area at NIMO (m²) | Filter area at NICO (m²) |
|---|---|---|---|
| CUNO 01-10 SP | 80 | 187.5 | 27.5 |
| CUNO 60-120 SP | 400 | 37.4 | 5.5 |

TABLE 7-continued

Filtration Train

| Filter | Capacity (L/m²) | Filter area at NIMO (m²) | Filter area at NICO (m²) |
|---|---|---|---|
| Pall Ultipor 0.2 µm | 2000 | 7.5 | 1.1 |
| Pall Ultipor 0.1 µm | 217 | 68 | 10 |

The optimal operating conditions for the centrifuge resulted in filter requirements as shown in Table 8.

TABLE 8

Filter Requirements

| Filter | Capacity (L/m²) | Filter area at NIMO (m²) | Filter area at NICO (m²) |
|---|---|---|---|
| CUNO 90-120 SP | 441 | 34 | 5 |
| Pall Ultipor 0.2 µm | 2000 | 7.5 | 1.1 |
| Pall Ultipor 0.1 µm | 160 | 93.8 | 13.8 |

The total filtration area is reduced substantially when using the proposed filter train. For cost comparisons, the following assumptions were used: the cost of the depth filters were assumed as 86 \$/m², irrespective of the grade used, the cost of the 0.2 µm filters was estimated at 320 \$/m² and the 0.1 µm filter costs were set to 340 \$/m². Using these estimates, costs estimates were calculated as shown in Table 9.

TABLE 9

Estimate of Filter Cost for 0.1 µm Final Filter

| | With centrifugation | | Filtration only | |
|---|---|---|---|---|
| Filter cost (\$) | NIMO | NICO | NIMO | NICO |
| CUNO 01-10 SP | — | — | 16125 | 2365 |
| CUNO 60-120 SP (filtration only) CUNO 90-120 SP (centrifuge) | 2925 | 430 | 3217 | 472 |
| Pall Ultipor 0.2 µm | 2400 | 352 | 2400 | 352 |
| Pall Ultipor 0.1 µm | 31875 | 4675 | 23181 | 3400 |
| Total Filter | 37200 | 5457 | 44923 | 6589 |
| Savings due to centrifuge | 17% | | | |

A large proportion of the filtration costs arises from the 0.1 µm absolute filters, which have been proposed to be omitted from the filter train. Use of such a tight grade filter may not be necessary in order to protect the first chromatography column. In fact, there are numerous companies in the industry, which do not use 0.1 µm filtration during harvest. In order to demonstrate the economic benefit of such a decision, the cost estimates were repeated for 0.2 µm filtration as the final grade.

TABLE 10

Estimate of Filter Cost for 0.2 µm Final Filter

| | With centrifugation | | Filtration only | |
|---|---|---|---|---|
| Filter cost (\$) | NIMO | NICO | NIMO | NIMO |
| CUNO 01-10 SP | — | — | 16125 | 2365 |
| CUNO 60-120 SP (filtration only) | 2925 | 430 | 3217 | 472 |

TABLE 10-continued

Estimate of Filter Cost for 0.2 μm Final Filter

| Filter cost ($) | With centrifugation | | Filtration only | |
|---|---|---|---|---|
| | NIMO | NICO | NIMO | NIMO |
| CUNO 90-120 SP (centrifuge) | | | | |
| Pall Ultipor 0.2 μm | 2400 | 352 | 2400 | 352 |
| Total Filter | 5325 | 782 | 21742 | 3189 |
| Savings due to centrifuge | 76% | | | |

Omission of the 0.1 μm final filter substantially reduces filtration costs and thereby increases the comparative benefit of centrifugation.

Example 2

Clarification of an NSO Cell Culture for Purification of Secreted Antibodies

A centrifuge was used in conjunction with depth filters to effect clarification of an NSO cell culture. The cells of the cell culture secrete an antibody of interest, such that the clarification process can be used as an initial step of antibody purification. Clarification includes use of a centrifuge followed by a series of depth filters, prefilters, and membrane filters, such that insoluble matter (including cells, cellular debris, and all other insoluble matter in the cell culture) is removed and the liquid centrate containing the antibodies is substantially clean. The clarity is typically described as 0.2 μm clarity, which refers to the pore size rating of the last filter in the serial assembly.

A clarification process was developed to accommodate clarification of NSO cell cultures having a solid matter of approximately 1% (wet weight/volume) and viability within the range from 3% to 100%. Centrifugation was performed inclusively within the range of 8000×g to 15000×g (g=acceleration due to gravity), which provided centrate turbidities of ≧25 NTU. At this level of turbidity, depth filter capacity was in the range of about 40 L/m² to greater than 400 L/m². The turbidity of the depth filter filtrate was in the range of about 1-15 NTU, resulting in filter loads in the range of 10 L/m² to 14000 L/m² on the downstream prefilters and membrane filters.

TABLE 11

Symbols and Abbreviations

| A | Equivalent settling area | m² |
|---|---|---|
| D | Particle diameter | M |
| E | Solids removal | |
| G | Gravitational constant | m/s² |
| G | Centrifugal acceleration | s⁻¹ |
| L | Bowl length | M |
| N | Number of disks in a stack | |
| η | Viscosity | kg/(m · s) |
| PCV | Packed cell volume | % |
| Q | Volumetric Flow | m³/s |
| R | Centrifuge bowl or disk radius | |
| $Re_d$ | Size recovery of particles of diameter d | |
| $\rho_l$ | Liquid density | kg/m³ |
| $\rho_s$ | Solids density | kg/m³ |
| φ | Conical half angle of a disk | |
| Σ | Sigma factor (area equivalent) | m² |
| t | Time | S |
| u | Fluid velocity | m/s |

TABLE 11-continued

Symbols and Abbreviations

| $V_{gd}$ | Settling velocity under gravity | m/s |
|---|---|---|
| $V_s$ | Terminal settling velocity | m/s |
| Ω | Angular speed | s⁻¹ |

REFERENCES

The references cited in the specification are incorporated herein by reference in their entirety as they supplement, explain, provide a background for or teach methodology, techniques and/or compositions employed herein.

Ambler, C. M. The theory of scaling up laboratory data for the sedimentation type centrifuge. *J. Biochem. Microbiol. Technol. Eng.* 1, 185-205 (1959).

Borgstrom, L., Carlson, C.-G., Inge, C., Lagerstedt, T. & Moberg, H. Pressure drop for flow in channels subjected to strong system rotation. *Applied Scientific Research* 53, 35-50 (1994).

Kempken, R., Preissmann, A. & Berthold, W. Assessment of a disk-stack centrifuge for use in mammalian cell separation. *Biotechnol. Bioeng.* 46, 132-138 (1995).

Leung, W. W.-F. *Industrial centrifugation technology* (Mc Graw Hill, New York, 1998).

Maybury, J. P., Hoare, M. & Dunnill, P. The use of laboratory centrifugation studies to predict performance of industrial machines: studies of shear-insensitive and shear-sensitive materials. *Biotechnol. Bioeng.* 67, 265-273 (2000).

Tebbe, H., Luetkemeyer, R., Gudermann, F., Heidemann, R. & Lehmann, J. Lysis-free separation of hybridoma cells by continuous disk stack centrifugation, *Cytotechnology* 22, 119-127 (1996).

What is claimed is:

1. A method for separating therapeutic proteins from an industrial scale cell sample comprising:
    (a) centrifuging the cell sample at a gravitational force of from about 8,000×g to about 15,000×g and a Q/Σ ratio of about 1×10⁻⁸ m/s, wherein the centrifugation separates the cells and cellular debris from the centrate which comprises the therapeutic proteins; and
    (b) applying the centrate to a depth filtration means so as to recover a filtrate which comprises the therapeutic proteins, wherein the depth filtration means is effective to separate remaining particulate matter from the filtrate comprising the therapeutic proteins.

2. The method of claim 1, wherein the gravitational force is in the range of about 8,000×g to about 12,000×g.

3. The method of claim 1, wherein the gravitational force is in the range of about 8,000×g to about 10,000×g.

4. The method of claim 1, wherein the gravitational force is in the range of about 10,000×g to about 15,000×g.

5. The method of claim 1, wherein the gravitational force is in the range of about 12,000×g to about 15,000×g.

6. A method for separating therapeutic proteins from an industrial scale cell sample, comprising:
    (a) centrifuging the cell sample at a gravitational force of from 8,000×g to 12,000×g and a Q/Σ ratio in the range of from 0.9×10⁻⁸ m/s to 2.8×10⁻⁸ m/s, wherein the centrifugation separates the cells and cellular debris from the centrate which comprises the therapeutic proteins; and
    (b) applying the centrate to a depth filtration means so as to recover a filtrate which comprises the therapeutic proteins, wherein the depth filtration means is effective to separate remaining particulate matter from the filtrate comprising the therapeutic proteins.

7. The method of claim 6, wherein the Q/Σ ratio is in the range of from $0.9 \times 10^{-8}$ to $1.8 \times 10^{-8}$ m/s.

8. The method of claim 6, wherein the Q/Σ ratio is in the range of from $1.8 \times 10^{-8}$ to $2.6 \times 10^{-8}$ m/s.

9. The method of claim 6 wherein the gravitational force is in the range of from 8,000×g to 9,600×g, wherein the Q/Σ ratio is in the range of from $0.9 \times 10^{-8}$ to $2.7 \times 10^{-8}$ m/s.

10. The method of claim 9, wherein the Q/Σ ratio is in the range of from $0.9 \times 10^{-8}$ to $1.8 \times 10^{-8}$ m/s.

11. The method of claim 9, wherein the Q/Σ ratio is in the range of from $1.8 \times 10^{-8}$ to $2.7 \times 10^{-8}$ m/s.

12. A method for separating therapeutic proteins from an industrial scale cell sample, comprising:
    (a) centrifuging the cell sample at a gravitational force of from 9,600×g to 15,000×g and a Q/Σ ratio in the range of from $0.9 \times 10^{-8}$ m/s to $2.8 \times 10^{-8}$ m/s, wherein the centrifugation separates the cells and cellular debris from the centrate which comprises the therapeutic proteins; and
    (b) applying the centrate to a depth filtration so as to recover a filtrate which comprises the therapeutic proteins, wherein the depth filtration means is effective to separate remaining particulate matter from the filtrate comprising the therapeutic proteins.

13. The method of claim 12, wherein the Q/Σ ratio in the range of from $0.9 \times 10^{-8}$ to $1.8 \times 10^{-8}$ m/s.

14. The method of claim 12, wherein the Q/Σ ratio is in the range of from $1.8 \times 10^{-8}$ to $2.8 \times 10^{-8}$ m/s.

15. The method of claim 12, wherein the gravitational force is in the range of from 12,000×g to 15,000×g, wherein the Q/Σ ratio is in the range of from $0.9 \times 10^{-8}$ to $2.8 \times 10^{-8}$ m/s.

16. The method of claim 15, wherein the Q/Σ ratio is in the range of from $0.9 \times 10^{-8}$ to $1.8 \times 10^{-8}$ m/s.

17. The method of claim 15, wherein the Q/Σ ratio is in the range of from $1.8 \times 10^{-8}$ to $2.8 \times 10^{-8}$ m/s.

18. The method of claim 12, wherein the gravitational force is in the range of from 9,600×g to 12,000×g, wherein the Q/Σ ratio is in the range of from $0.9 \times 10^{-8}$ to $2.7 \times 10^{-8}$ m/s.

19. The method of claim 18, wherein the Q/Σ ratio is in the range of from $0.9 \times 10^{-8}$ to $1.8 \times 10^{-8}$ m/s.

20. The method of claim 18, wherein the Q/E ratio is in the range of from $1.8 \times 10^{-8}$ to $2.7 \times 10^{-8}$ m/s.

\* \* \* \* \*